(12) United States Patent
Case et al.

(10) Patent No.: US 8,252,043 B2
(45) Date of Patent: Aug. 28, 2012

(54) REMOVABLE COVERING FOR IMPLANTABLE FRAME PROJECTIONS

(75) Inventors: Brian C. Case, Lake Villa, IL (US); Charles W. Agnew, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 2 days.

(21) Appl. No.: 12/484,601

(22) Filed: Jun. 15, 2009

(65) Prior Publication Data
US 2009/0254174 A1 Oct. 8, 2009

Related U.S. Application Data

(63) Continuation of application No. 11/583,395, filed on Oct. 19, 2006, now Pat. No. 7,563,277.

(60) Provisional application No. 60/729,559, filed on Oct. 24, 2005.

(51) Int. Cl.
*A61F 2/06* (2006.01)
(52) U.S. Cl. ...................... 623/1.38; 623/1.15
(58) Field of Classification Search ................. 623/1.14, 623/1.15, 1.24, 1.44–1.46; *A61F 2/24, 2/06*
See application file for complete search history.

(56) References Cited

U.S. PATENT DOCUMENTS

| | | | |
|---|---|---|---|
| 4,902,508 A | 2/1990 | Badylak et al. | |
| 5,554,389 A | 9/1996 | Badylak et al. | |
| 5,779,729 A | 7/1998 | Severini | |
| 5,800,526 A | 9/1998 | Anderson et al. | |
| 5,993,844 A | 11/1999 | Abraham et al. | |
| 6,099,567 A | 8/2000 | Badylak et al. | |
| 6,206,931 B1 | 3/2001 | Cook et al. | |
| 6,375,989 B1 | 4/2002 | Badylak et al. | |
| 6,494,909 B2 | 12/2002 | Greenhalgh | |
| 7,186,789 B2 | 3/2007 | Hossainy et al. | |
| 7,258,697 B1 * | 8/2007 | Cox et al. | 623/1.16 |
| 2004/0137042 A1 | 7/2004 | Hiles et al. | |
| 2004/0167619 A1 | 8/2004 | Case et al. | |
| 2004/0180042 A1 | 9/2004 | Cook et al. | |
| 2004/0186558 A1* | 9/2004 | Pavcnik et al. | 623/1.24 |
| 2004/0243222 A1* | 12/2004 | Osborne et al. | 623/1.24 |
| 2005/0043708 A1 | 2/2005 | Gleeson et al. | |

FOREIGN PATENT DOCUMENTS

| | | |
|---|---|---|
| WO | WO 98/25636 A1 | 6/1998 |
| WO | WO 98/25637 A1 | 6/1998 |
| WO | WO 98/26291 A1 | 6/1998 |

* cited by examiner

*Primary Examiner* — Thomas J Sweet
*Assistant Examiner* — Jason-Dennis Stewart
(74) *Attorney, Agent, or Firm* — Buchanan Nipper

(57) ABSTRACT

The disclosure relates to medical devices for implantation in a body vessel, and methods of using and making the same. A medical device can include a frame with one or more projections each having at least one edge extending from the surface of the frame, and a biocompatible, water-soluble removable material coated over at least a portion of the at least one edge. The projections can be barbs positioned to engage the interior wall of a body vessel or to attach a material, such as a valve leaflet or graft, to the frame. The removable material can be dissolved within a body vessel upon implantation, thereby exposing the at least one edge. Methods of making an implantable medical device and methods of treating a subject are also disclosed.

21 Claims, 8 Drawing Sheets

REMOVABLE COVERING FOR IMPLANTABLE FRAME PROJECTIONS

PRIORITY CLAIM

This application is a continuation of U.S. patent application Ser. No. 11/583,395, filed Oct. 19, 2006, which claims the benefit of provisional U.S. Patent Application Ser. No. 60/729,559, filed Oct. 24, 2005, both of which are incorporated herein by reference in their entirety.

TECHNICAL FIELD

The present disclosure relates to medical devices. More particularly, the disclosure relates to medical devices for implantation in a body vessel comprising frame projections covered by a removable material.

BACKGROUND

Various implantable medical devices can be deployed within the lumen of a body vessel using minimally-invasive transcatheter techniques. For example, implantable medical devices can function as a replacement valve, or restore native valve function. Such devices can include an expandable frame configured for implantation in the lumen of a body vessel, such as a vein. Implantable valves can further comprise features that provide a valve function, such as opposable leaflets.

Many implantable medical devices include an implantable frame having a plurality of projections extending from the surface of the frame, such as barbs or cutting edges. The projections can have one or more sharp beveled edges that can perform beneficial functions upon implantation within a body vessel, such as retaining a valve leaflet or graft material attached to the medical device or securing the medical device within a body vessel by puncturing and engaging the interior surface of a body vessel. Before implantation within the body vessel, however, projections having one or more beveled edges can inadvertently and undesirably contact and even damage other portions of the medical device, a delivery system or the body vessel.

There exists a need in the art for an implantable medical device including a removable material to form a protective covering over or around one or more edges of a projection from a medical device frame. Removable materials that dissolve readily on implantation within a body vessel but retain a desired level of durability prior to implantation are particularly desirable. For example, a removable material can be coated over a barb extending from an implantable frame, and then dissolved rapidly upon implantation in a body vessel.

SUMMARY

The disclosure relates to removable coverings for sharp edges of an implantable medical device frame, such as a barb or other sharp frame projection, prior to implantation of the frame in a body vessel. An implantable frame can be an expandable stent or a portion of a prosthetic valve. The removable covering is preferably a biocompatible water-soluble material positioned over a sharp edge of a projection extending from the surface of the implantable frame. The removable material can form a coating over the surface of the frame, or any portion thereof that includes one or more sharp edges. The projection can have any desired function, but is preferably adapted to engage the interior surface of a body vessel (such as a barb) or to retain a material attached to the frame (such as a valve leaflet). The implantable frame is preferably expandable from a compressed state for delivery via transcatheter implantation and a radially expanded state for deployment from a catheter within a body vessel.

Desirably, the removable material can protect the interior of the body vessel, material attached to the implantable frame such as valve leaflets, or portions of the delivery system from potentially damaging inadvertent contact with a sharp edge of a frame prior to and during deployment of the frame in a body vessel. The removable material is preferably a water-soluble material with sufficient durability to cover a sharp edge during delivery and placement within the body vessel. The removable material preferably has a sufficient solubility within a body vessel for the removable material to dissolve rapidly enough during a transcatheter delivery procedure to expose the sharp edge during deployment of the implantable frame prior to removal of a delivery catheter. The removable material can be attached to itself or to the frame by any suitable means, including the application of tissue adhesives, cross-linkers, adhesives or natural materials such as fibrin.

The removable material preferably has a thickness sufficient to provide a desirable level of durability, but thin enough to permit sufficiently rapid dissolution of the removable material within a body vessel. For example, the removable material can have a thickness of between about 10 μm and 1 mm. The removable material can form a coating over the entire surface of an implantable frame, or only over portions of the frame such as over projections or only the edges of projections from the frame.

Desirably, the removable material covers the edges of one or more barb projections extending from surface of the implantable frame. The frame projections can have any suitable size or cross-sectional shape. For example, a barb or other projection can have a substantially triangular, substantially square, substantially rectangular, substantially elliptical, or substantially semi-circular cross-sectional shape. Preferably, the cross-sectional area of the base of the projection is less than about 10 mm$^2$.

Preferably, the medical devices are configured as implantable valves, stent grafts or stents. Implantable valves and stent grafts can include a radially expandable frame and a material attached to the frame. In an implantable valve, the material can form one or more moveable valve leaflets for regulating the flow of fluid within a body vessel. In a stent graft, a material can be attached around the outer surface of the implantable frame. Preferably, the material is a remodelable material, such as small intestine submucosa (SIS).

In one example, a medical device is provided for implantation in a body vessel. The medical device preferably includes an implantable frame having a surface that includes a plurality of projections extending from the surface, the plurality of projections each having at least one beveled edge and including a first projection comprising a first beveled edge, the first projection having a cross-sectional area at the intersection of the projection and the surface that is less than about 10 mm$^2$; and a biocompatible removable material covering a first portion of the surface of the implantable frame including the first edge of the first projection. In one aspect, the removable material is water-soluble. The plurality of projections may be configured as barbs configured to engage the wall of a body vessel. The surface may include a first surface portion covered by the removable material and having a surface area that is less than about 10 mm$^2$. The surface of the implantable frame may also include a second portion that is not covered by the removable material and does not include a projection. The removable material covering preferably has a thickness of between about 1 μm and 1 mm thick. In one aspect, the implantable frame has a tubular configuration that is moveable from a radially compressed state to a radially expanded state. The implantable frame can be made from any suitable material, but preferably includes a material selected from the group consisting of: a nickel-titanium alloy, a cobalt-chromium alloy, and stainless steel. Desirably, the medical device is an implantable valve further comprising at least one valve leaflet attached to the implantable frame, the implantable frame comprising a plurality of struts and bends defining a substantially cylindrical lumen and having a plurality of projections configured as barbs attached to the implantable frame.

In another example, a method of making an implantable medical device comprises providing a frame having one or more projections with at least one sharp edge. The method may also comprise the step of applying a removable material to the at least one sharp edge at a desired thickness.

In yet another example, a method of treating a subject comprises implanting a medical device at a point of treatment, where the medical device comprises a frame and a removable material coated over at least one sharp edge of a projection from the frame.

Other systems, methods, features and advantages will be, or will become, apparent to one with skill in the art upon examination of the following figures and detailed description. It is intended that all such additional systems, methods, features and advantages be included within this description, be within the scope of the disclosure, and be protected by the following claims.

BRIEF DESCRIPTION OF THE DRAWINGS

The medical device may be better understood with reference to the following drawings and description. The components in the figures are not necessarily to scale, emphasis instead being placed upon illustrating the principles of the disclosure. Moreover, in the figures, like referenced numerals designate corresponding parts throughout the different views.

DETAILED DESCRIPTION

Figure 1:
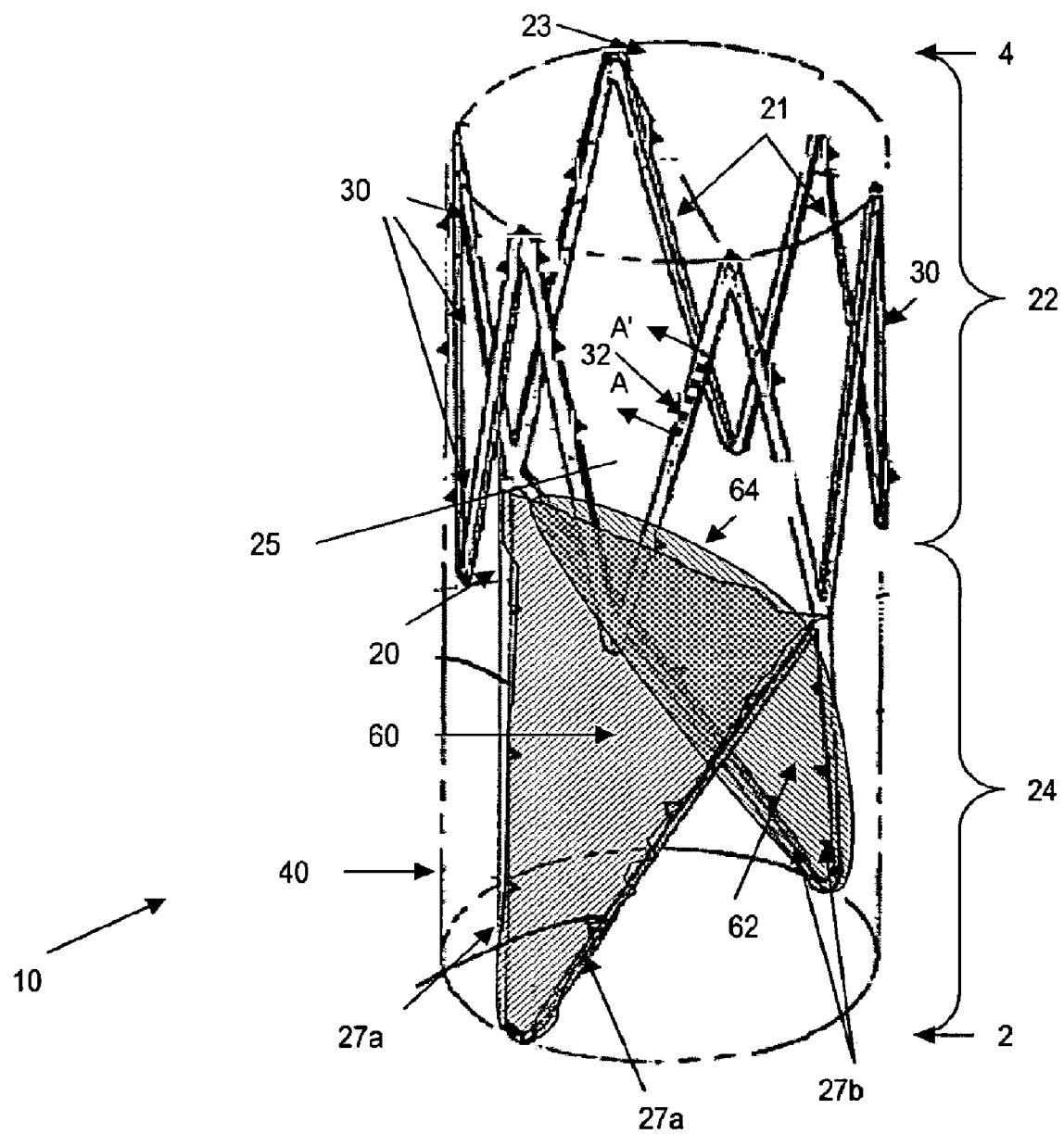
FIG. 1 is a perspective view of a first implantable medical device including a plurality of barb projections covered with a removable material.

The following detailed description and appended drawings describe and illustrate various examples of the present disclosure. The disclosure provides medical devices for implantation in a body vessel, methods of making the medical devices, and methods of treatment that utilize the medical devices. More specifically, the disclosure relates to a medical device comprising a removable material contacting at least one edge of an implantable frame. The edge is preferably a beveled edge formed by the intersection of at least two planar surfaces of a projection from the surface at an angle other than 90-degrees with respect to one another. Preferably, the beveled edge is a sharpened edge adapted to engage the wall of a body vessel.

Unless otherwise defined, all technical and scientific terms used herein have the same meaning as commonly understood by one of ordinary skill in the art to which this disclosure pertains. In case of conflict, the present document, including definitions, will control. Preferred methods and materials are described below, although methods and materials similar or equivalent to those described herein can be used in the practice or testing of the present disclosure. All publications, patent applications, patents and other references mentioned herein are incorporated by reference in their entirety. The materials, methods, and examples disclosed herein are illustrative only and not intended to be limiting.

DEFINITIONS

As used herein the terms "comprise(s)," "include(s)," "having," "has," "contain(s)," and variants thereof, are intended to be open-ended transitional phrases, terms, or words that do not preclude the possibility of additional acts or structure.

As used herein, the term "body vessel" means any tube-shaped body passage lumen that conducts fluid, including but not limited to blood vessels such as those of the human vasculature system, biliary ducts and ureteral passages.

As used herein, the term "implantable" refers to an ability of a medical device to be positioned at a location within a body, such as within a body vessel. Furthermore, the terms "implantation" and "implanted" refer to the positioning of a medical device at a location within a body, such as within a body vessel.

As used herein, "endolumenally," "intraluminally" or "transluminal" all refer synonymously to implantation placement by procedures where the medical device is advanced within and through the lumen of a body vessel from a remote location to a target site within the body vessel. In vascular procedures, a medical device will typically be introduced "endovascularly" using a catheter over a guidewire under fluoroscopic guidance. The catheters and guidewires may be introduced through conventional access sites to the vascular system, such as through the femoral artery, or brachial and subclavian arteries, for access to the coronary arteries.

A "biocompatible" material is a material that is compatible with living tissue or a living system in a manner consistent with an intended treatment, for example by not being toxic or injurious to an undesirable extent, or not causing undesirable levels of immunological rejection.

The term "frame" refers to any biocompatible frame suitable for implantation within a body vessel. Preferably, a frame can expand from a radially compressed, or unexpanded, delivery configuration to one or more radially expanded deployment configurations, for example through self-expansion or balloon expansion of the frame. The expanded configuration can have any suitable cross-sectional configuration, including circular or elliptical. In one example, the frame can be oriented along the longitudinal axis of a body vessel in the expanded or compressed configurations.

As used herein, a "point of attachment" refers to a location where two adjacent surfaces are joined together.

The terms "remodelable" or "bioremodelable" refer to the ability of a material to allow or induce host tissue growth, proliferation or regeneration following implantation of the tissue in vivo. Remodeling can occur in various microenvironments within a body, including without limitation soft tissue, a sphincter muscle region, body wall, tendon, ligament, bone and cardiovascular tissues. Upon implantation of a remodelable material, cellular infiltration and neovascularization on or within the remodelable material are typically observed over a period of about five days to about six months or longer, as the remodelable material acts as a matrix for the ingrowth of adjacent tissue with site-specific structural and functional properties. The remodeling phenomenon which occurs in mammals following implantation of submucosal tissue typically includes rapid neovascularization and early mononuclear cell accumulation. Mesenchymal and epithelial cell proliferation and differentiation are typically observed by one week after in vivo implantation and extensive deposition of new extracellular matrix occurs almost immediately. In some examples, fluid contacting autologous cells on an implanted remodelable material can affect the growth of autologous tissue on the implanted remodelable material.

Medical Device Configurations

FIG. 1 is a perspective view of an implantable medical device including a plurality of barb projections covered with a removable material. The medical device 10 is a valve including a radially expandable frame 20 shown in a radially expanded state within a segment of a body vessel 40, and a pair of valve leaflets 60, 62 attached to the frame 20. The outer surface of the frame 25 contacting the body vessel 40 can include a plurality of projections 30 configured as barbs that extend from the frame 20 and are configured to engage the wall of the body vessel 40. Each projection 30 includes a sharp beveled edge and is covered by a removable covering before implantation in the body vessel 40. The frame 20 can be formed from a self-expanding material, such as a superelastic nickel-titanium alloy, that exerts an outward radial force against the body vessel 40. The frame 20 is delivered in a radially compressed state by a delivery catheter and permitted to expand by self-expansion at the point of treatment. The projections 30 are configured to engage the interior wall of a body vessel 40 to secure the frame 20 and prevent migration of the implant. The projections can have any suitable size or cross-sectional shape. For example, a barb or other projection can have a substantially triangular, substantially square, substantially rectangular, substantially elliptical, or substantially semi-circular cross-sectional shape. Preferably, the cross-sectional area of the base of the projection is less than about 10 mm$^2$, preferably about 0.1-1 mm$^2$. Each side of the base of the projection can be, for example, about 0.01-10 mm, but is preferably about 0.5-2 mm on each side. Suitable cross-sectional areas of a barb projection can be on the order of 0.1-10 mm$^2$, preferably about 0.5-5 mm$^2$, and more preferably about 1 mm$^2$.

The medical device 10 includes a plurality of interconnected struts 21 and bends 23, and includes a serpentine ring segment or hoop member 22 at the distal end and a "double-V" shaped proximal frame portion 24. A pair of valve leaflets 60, 62 are attached to a first pair of struts 27a and a second pair of struts 27b. The distal end of the pair of valve leaflets 60, 62 are opposably positioned to define a valve orifice 64 that has an open position and a closed position. The valve orifice opens to permit fluid to flow from the proximal end 2 of the medical device 10 to the distal end 4, and closes to substantially prevent fluid flow in the opposite direction. The valve leaflets 60, 62 can be formed from a material that is flexible enough to move the valve orifice between the open and closed positions in response to changes of fluid flow or pressure within the medical device 10. Examples of suitable valve material include extracellular matrix materials (ECM) such as small intestine submucosa and biostable polymer materials such as PTFE and ePTFE.

Figure 2A:
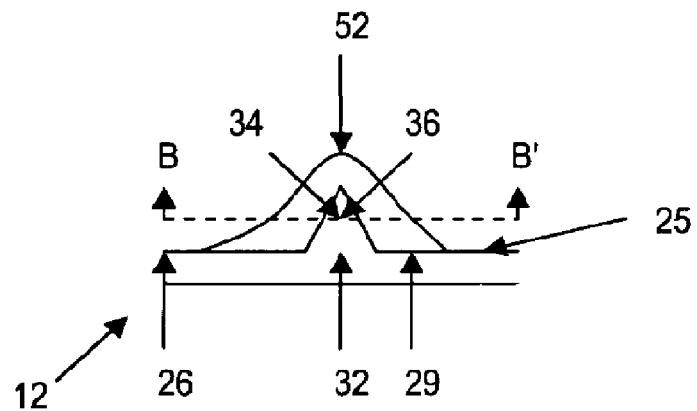
FIG. 2A is side view of a covered barb projection from the implantable frame of the first medical device shown in FIG. 1.
Figure 2B:
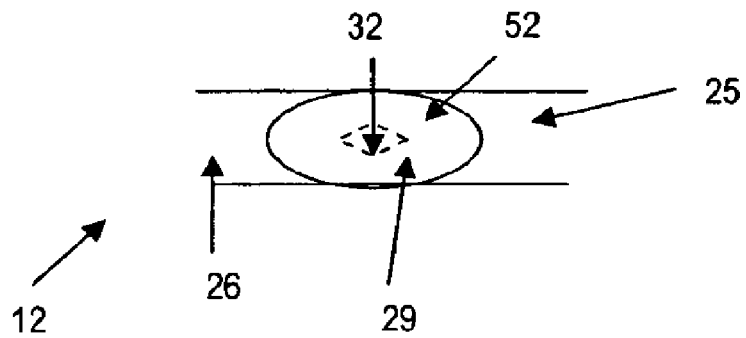
FIG. 2B is a cross-sectional view of the covered barb projection from the implantable frame of the first medical device shown in FIG. 1 and FIG. 2A.

FIG. 2A is side view of a covered barb projection from the implantable frame in FIG. 1. FIG. 2A shows frame segment 12, a cross section along the line A-A' in FIG. 1 of the frame 20, which includes a projection 32. The projection 32 includes a first sharp beveled edge 34 and a second sharp beveled edge 36 meeting in a point. The projection 32 is covered by a rounded removable material 52. Alternatively, the removable material 52 can be positioned adjacent to, rather than covering, a projection 30. For example, a removable material can be deposited adjacent to a projection 30 on the outer surface 25 of the frame, and can extend farther from the frame surface than the projection 30. The outer surface 25 of the frame segment 12 includes an uncovered portion 26 that is not coated with the removable material 52 and a covered portion 29 that is covered with the removable material. Alternatively, the covered portion 29 of the frame segment 12 can be positioned adjacent to the projection 32, while the uncovered portion 26 can include the barb projection 32. FIG. 2B is a cross-sectional view of the covered barb projection 32 from the implantable frame 12 along the line B-B' in FIG. 2A. FIG. 2B shows frame segment 12, along the cross section line B-B' in FIG. 2A of the frame segment barb projection 32, which includes a projection 32. The projection 32 is covered by a removable material 52. The outer surface 25 of the frame segment 12 includes an uncovered portion 26 that is not coated with the removable material 52 and a covered portion 29 that is covered with the removable material.

Figure 3:
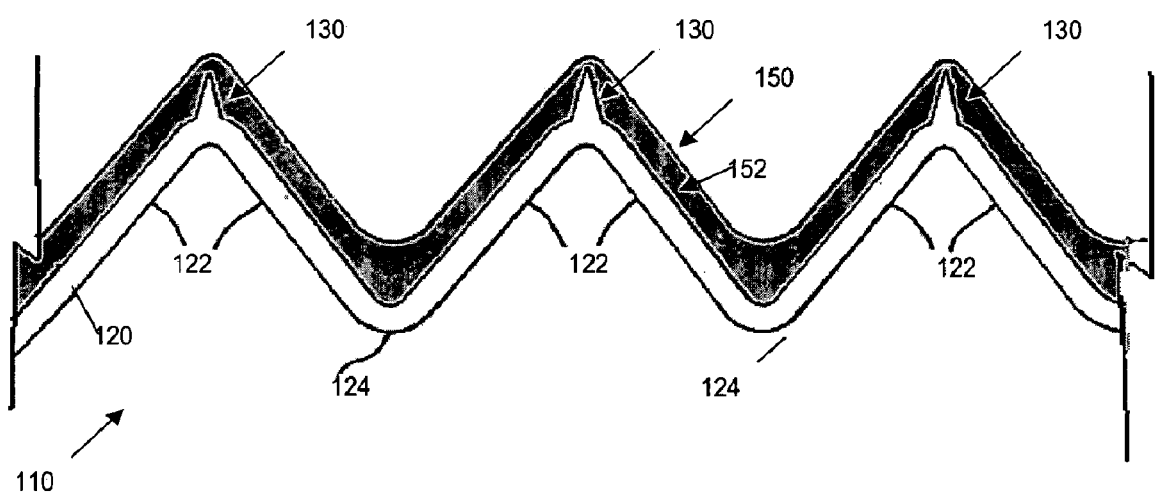
FIG. 3 is a side view of a segment of an implantable frame portion of a second medical device having a covering of a removable material.

FIG. 3 is a longitudinal cross sectional view of a segment of a second implantable frame having a covering of a removable material. The segment 110 of the implantable frame 120 comprises a plurality of interconnected struts 122 and bends 124. The frame 120 also includes a plurality of barbs 130 extending from certain bends. A coating layer 150 of removable material 152 covers one surface of the frame segment, enclosing the barbs 130. Upon implantation in a body vessel, the coating layer 150 can be rapidly dissolved by exposure to bodily fluids, exposing the barbs 130. Alternatively, the coating layer 150 can be thicker than the height of the barbs 130, and can be positioned intermittently to cover portions of the frame between the barbs 130, while leaving the barbs exposed 130. In this manner, the coating 150 can be configured to protect tissue from contacting the barbs 130 prior to removal of the removable material 152.

Figure 4:
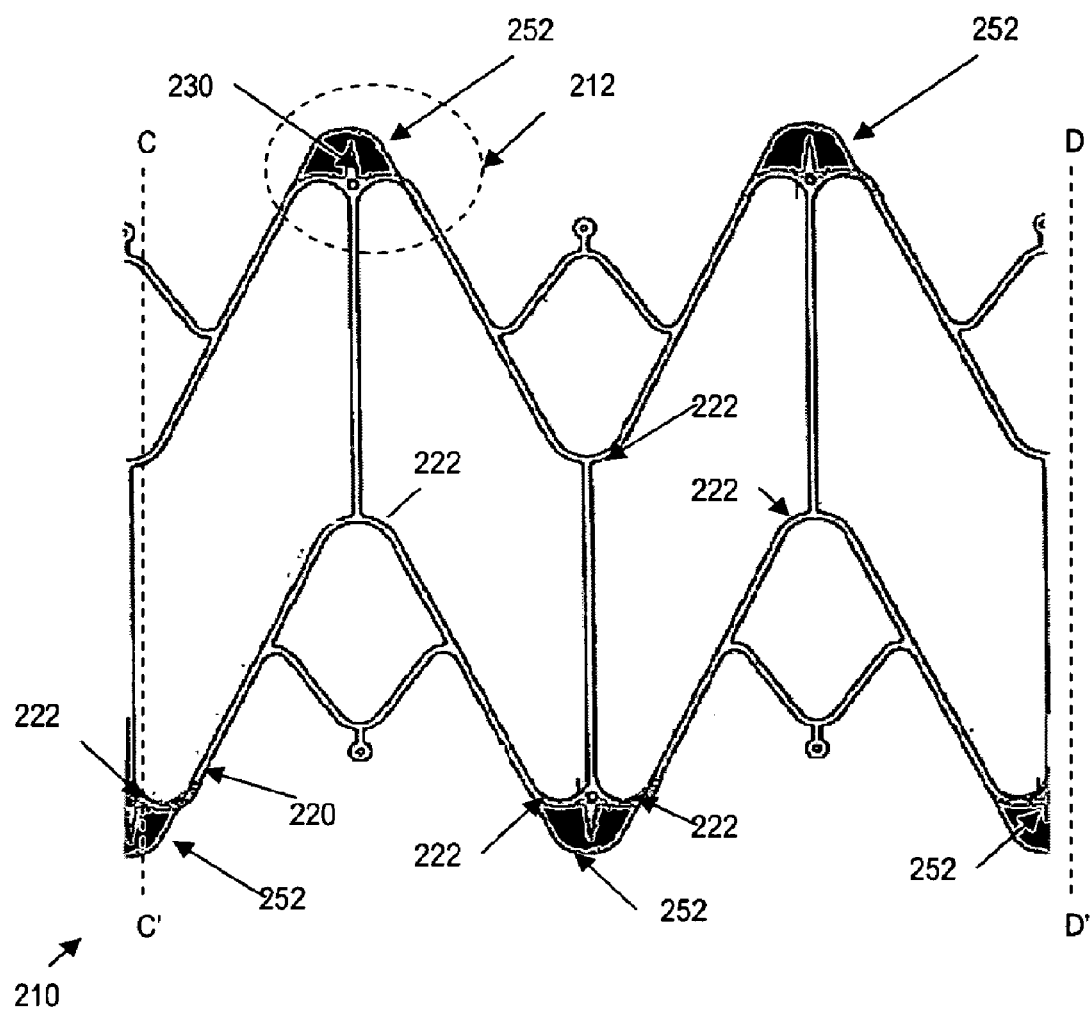
FIG. 4 is a flat plan view of an implantable frame of a third medical device having a removable material attached to a portion of the frame.
Figure 5:
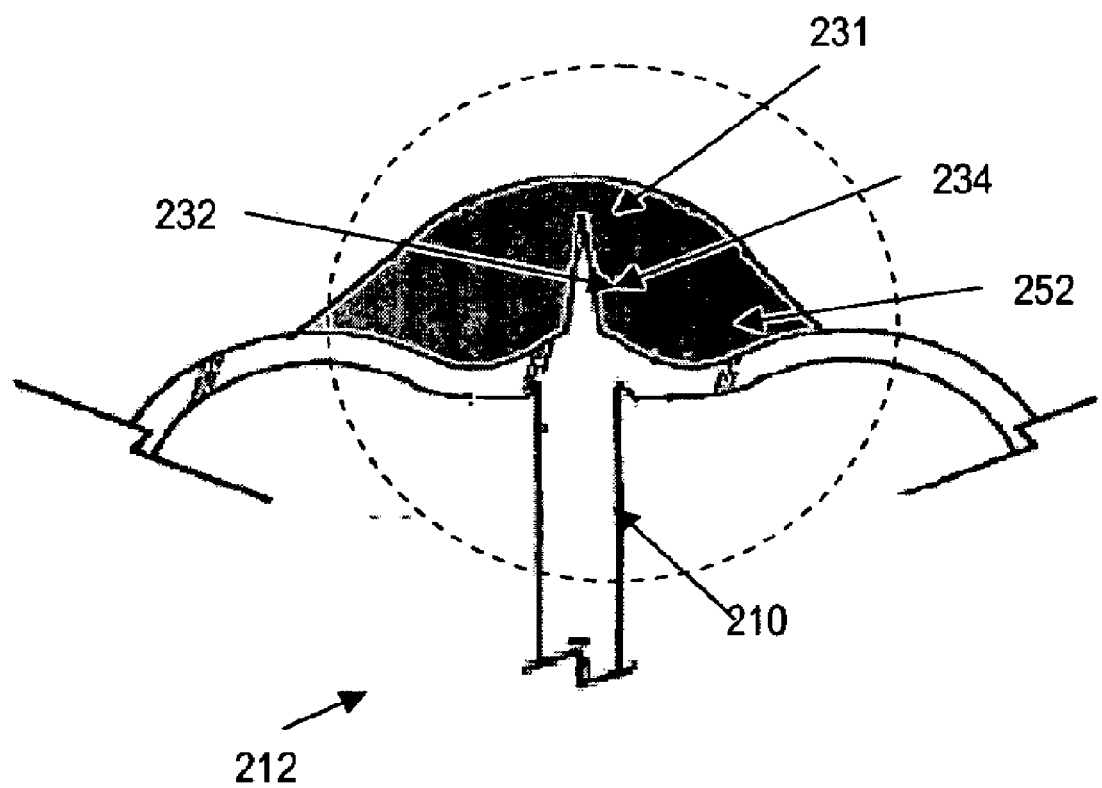
FIG. 5 is detailed view of a portion of the implantable frame of the third medical device, also depicted in FIG. 4.

FIG. 4 is a flat plan view of a third implantable frame having a removable material attached to a portion of the frame. The implantable frame 210 is formed when the C-C' line is placed coincident to the D-D' line, to form a tubular frame defining a cylindrical central lumen. The frame 210 includes a plurality of interconnected struts 220 and bends 222, and includes a plurality of barbs 230 attached to certain bends 222. The plurality of barbs 230, including a first barb 231, are covered by a removable material 252 that dissolves upon contact with fluid within a body vessel as the frame 210 is being implanted therein. A portion 212 of the implantable frame 210 is shown in FIG. 5. FIG. 5 is a detailed view of a portion of the frame 210 including the first barb 231. The barb 231 projects from the frame 210 and includes a first edge 232 and a second edge 234. The barb 230 is enclosed in the removable material 252.

Figure 6:
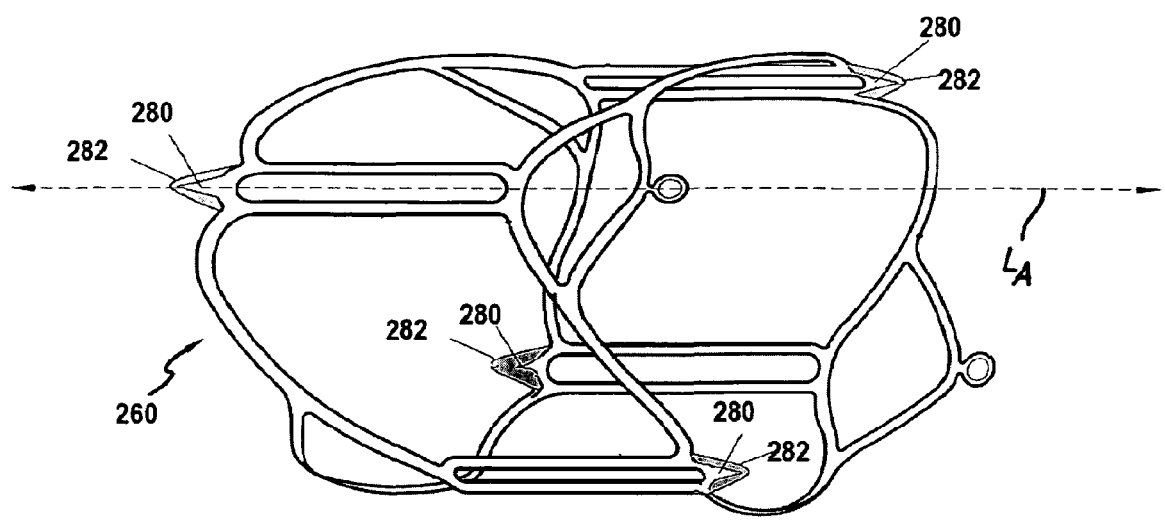
FIG. 6 is a perspective view of a fourth medical device including a plurality of projections covered by a removable material.

FIG. 6 is a perspective view of a fourth implantable frame 260 in a radially expanded state comprising a plurality of sharpened projections 280 covered by a removable material 282. The sharpened projections 280 are configured to engage the wall of a body vessel upon expansion of the frame 260 and after dissolution of the removable material 282 within a body vessel. Alternative examples include any implantable medical device having a portion of the surface, such as a sharp beveled edge of a valvulotome that can be covered with a removable material before deployment within a body vessel.

Removable Material

A variety of removable materials may be used to cover an implantable frame projection. Preferably the removable material is durable, solid, and flexible at room temperature, and dissolves readily when exposed to blood under normal blood temperatures and pH. The rate of dissolution of the removable materials can be varied by changing the molecular weights of the removable material. Typically, the lower the molecular weight of a removable material polymer, the faster the removable material will dissolve. The molecular weight of the polymer can be selected to provide a desired rate of dissolution and durability. Some polymers, such as chondroitin sulfate, may occur in nature with a molecular weight as high as 25,000, while others, such as hydroxypropylmethyl cellulose might be as high as 1,000,000. Hyaluronate may have a molecular weight as great as 8,000,000. Preferably, the removable material is a water-soluble polymer that it rapidly imbibes water and softens and/or dissolves within a aqueous substance. The molecular weight of the polymer should be high enough so that the wet polymer has enough strength and film integrity remain intact during delivery of the medical device through a body vessel, and low enough so that the removable material will dissolve rapidly during deployment of the medical device. Varying the thickness or adding perforations will also increase the rate of dissolution of the removable material materials.

In a first aspect, the removable material comprises cellulose or a cellulose-based material. Suitable cellulosic polymers include: microcrystalline cellulose, cellulose alkyl ethers, carboxymethyl cellulose, and cellulose alkyl esters. Preferred cellulose alkyl ethers include: methylcellulose, ethyl cellulose, hydroxymethyl cellulose, hydroxyethyl cellulose, hydroxypropyl cellulose, hydroxypropylmethyl cellulose, hydroxypropyl methyl cellulose (MPMC) and carboxymethyl cellulose. Preferred cellulose alkyl esters include: cellulose acetophthalate, cellulose acetate, cellulose acetate phthalate (CAP), hydroxypropyl methylcellulose phthalate (HPMCP), hydroxyethyl cellulose, and hydroxypropyl methylcellulose acetate succinate (HPMCAS). Other naturally occurring polymers, such as chondroitin sulfate, may also be used as a removable material. Still other suitable removable material materials are the water-soluble cellulose mixed ethers disclosed in U.S. Pat. No. 4,358,587 to Brandt et al., incorporated herein by reference.

In a second aspect, the removable material comprises a suitable vinyl polymer, such as polyvinylpyrolidone (PVP), polyvinyl alcohol (PVA), crosslinked PVP, PVA or PVA/PVP co-polymers. The removable material may also include a polyacrylamide, a poly(methylvinyl ether), or polyacrylic acid.

In a third aspect, the removable material may also include a polymer comprising polyethylene or polyacrylic acid. For example, the removable material is preferably a polyethyleneoxide or poly(ethylene glycol) (PEG), having a weight average molecular weight in the range from 1000 to about 10,000 (preferably 8000). The removable material may also include the removable material comprises one or more esters of poly(meth)acrylic acid where the ester group may be represented by the formula—OR in which the R moiety is sufficiently small (e.g., methyl or ethyl or other C1 or C2 type of moiety) so that the polymer is water soluble; similar esters of polyvinyl alcohol; combinations of these, and the like. Most preferably, the water soluble material is PEG, more preferably PEG having a weight average molecular weight of about 8000. Hyaluronate may also be used as a removable material.

In a fourth aspect, the removable material may comprise a carbohydrate or starch, such as mannitol, pullulan (.alpha.-1, 4-;.alpha.-1,6-glucan), chitin, chitosan, polysaccharides such as pectin and elsinan, or starches and modified starches such as maltodextrin, amylose, high amylose starch, hydroxypropylated high amylase starch, acid and enzyme hydrolyzed corn and potato starches.

In a fifth aspect, the removable material may include suitable natural gums such as gum arabic, guar gum, locust bean gum, carrageenan gum, acacia, karaya, ghatti, tragacanth agar, tamarind gum, and xanthan gum. The removable material may also include gelatins, seaweed extracts such alginates (propylene glycol alginate, sodium alginate and the like), carrageenans or plant extracts such as konjac, pectin or arabinogalactan.

In a sixth aspect, the removable material can be applied to a portion of the medical device that is modified to permit attachment of the removable material. Preferably, projections from the surface of the medical device that include a beveled edge can be treated to permit adhesion of a removable material. In particular, beveled edges can be plasma pre-treated and coated with an amine-containing material, to which a water soluble polymer can be attached. For example, the plasma treated surface may be coated with a material containing amine groups, such as polyethyleneimine (PEI). Alternatively, a beveled edge of a projection from the surface of the medical device can be treated with a highly adherent material, such as acrylic acid polymers or copolymers, to promote the adherence of the amine groups to the substrate. Subsequently, the treated surface can be contacted with an aldonic acid and a coupling agent, such as a water-soluble carbodiimide. One preferred water-soluble carbodiimide is 1-ethyl-3-(3-dimethylaminopropyl)carbodiimide (EDC). The pH of the mixture is adjusted until the pH stabilizes. Then the mixture is brought into contact with the substrate, at room temperature. Components of the aldonic acid and the coupling agent may be reacted with the amine groups on the coating over the beveled edges, such that the beveled edges become coated with aldonic acid amide. The components which do not form part of the aldonic acid amide can be washed away and discarded. Other examples of aldonic acid-amine coatings are disclosed in U.S. Pat. No. 6,187,369 (Beavers).

Additives may also be added to affect desired properties of the removable material. For example, plasticizers are known in the art to increase flexibility when added to the removable material. Plasticizers include glycerol, sorbitol, polyethylene glycol, polypropylene glycol or sugars (glucose, maltodextrins, acetylated monoglycerides, citric or lactic acid esters). Brittleness may be reduced by adding esters of fatty acids and glycerol, examples of which include: glycerol monofatty acid esters, glycerol acetate fatty acid esters, glycerol lactate fatty acid esters, glycerol citrate fatty acid esters, glycerol succinate fatty acid esters, glycerol diacetyltartrate fatty acid esters and glycerol monoacetate. Other derivatives of the monoglyceride reacted with acetic acid, lactic acid, citric acid, succinic acid or diacetyltartaric acid may also be included in the ester of a fatty acid and glycerol.

Valve Leaflet or Graft Materials

A variety of materials can be attached to an implantable frame, for example to form a valve leaflet or a stent graft, including naturally derived materials, and synthetic materials.

In one aspect, the medical device includes a remodelable material attached to a frame. Preferably, the implantable medical device includes a valve leaflet or graft material comprising a remodelable material. Examples of suitable natural materials include remodelable materials, such as collagen and extracellular matrix (ECM) material. Small intestine submucosa (SIS) is particularly well-suited as a material, such as to form valve leaflets. Submucosal tissue can be obtained from warm-blooded tissues including the alimentary, respiratory, intestinal, urinary or genital tracts of warm-blooded vertebrates, including without limitation: intestinal submucosa, stomach submucosa, urinary bladder submucosa, and uterine submucosa. Other examples of ECMs are pericardium, stomach submucosa, liver basement membrane, urinary bladder submucosa, tissue mucosa, and dura mater. Information as to submucosa materials useful as ECM materials herein can be found in U.S. Pat. Nos. 4,902,508; 5,554,389; 5,993,844; 6,206,931; 6,099,567; and 6,375,989, as well as published U.S. Patent Applications US2004/0180042A1 and US2004/0137042A1, which are all incorporated herein by reference. For example, the mucosa can also be derived from vertebrate liver tissue as described in WIPO Publication, WO 98/25637, based on PCT application PCT/US97/22727; from gastric mucosa as described in WIPO Publication, WO 98/26291, based on PCT application PCT/US97/22729; from stomach mucosa as described in WIPO Publication, WO 98/25636, based on PCT application PCT/US97/23010; or from urinary bladder mucosa as described in U.S. Pat. No. 5,554,389; the disclosures of all are expressly incorporated herein.

Preferably, the source tissue for the ECM material is a submucosal tissue, such as tela submucosa, that is disinfected prior to delamination by the preparation disclosed in US Patent Application US2004/0180042A1 by Cook et al., published Sep. 16, 2004 and incorporated herein by reference in its entirety. Most preferably, the tunica submucosa of porcine small intestine is processed in this manner to obtain the ECM material. Other disclosures of methods for the isolation of ECM materials include the preparation of intestinal submucosa described in U.S. Pat. No. 4,902,508, the disclosure of which is incorporated herein by reference. Urinary bladder submucosa and its preparation are described in U.S. Pat. No. 5,554,389, the disclosure of which is incorporated herein by reference. Stomach submucosa has also been obtained and characterized using similar tissue processing techniques, for example as described in U.S. patent application Ser. No. 60/032,683 titled STOMACH SUBMUCOSA DERIVED TISSUE GRAFT, filed on Dec. 10, 1996, which is also incorporated herein by reference in its entirety.

In another aspect, the medical device includes a synthetic material attached to a frame. The synthetic material is preferably a biocompatible polymer. For instance, the implantable medical device may include a valve leaflet or graft material comprising a synthetic material, or a composite material including a synthetic material and a remodelable material. Examples of suitable synthetic materials include polymeric materials, such as polypropylene, polyurethane, expanded polytetrafluoroethylene (ePTFE), polyurethane (i), polyethylene terephthalate (PET), silicone, latex, polyethylene, nylon, polytetrafluoroethylene, polyimide, polyester, and mixture thereof.

Implantable Frames

The medical device can include an implantable frame with one or more projections. The frame can have any suitable configuration. The specific implantable frame chosen will depend on several considerations, including the size and configuration of the vessel and the size and nature of the medical device. The frame can perform any desired function, including a stenting function or a valve support function. The frame configuration may be selected based on several factors, including the vessel in which the medical device is being implanted, the axial length of the treatment site, the inner diameter of the body vessel, and the desired delivery method for placing the support structure. Those skilled in the art can determine an appropriate stent based on these and other factors. The implantable frame can be sized so that the expanded configuration is slightly larger in diameter that the inner diameter of the vessel in which the medical device will be implanted. This sizing can facilitate anchoring of the medical device within the body vessel and maintenance of the medical device at a point of treatment following implantation.

Suitable implantable frames can also have a variety of configurations, including braided strands, helically wound strands, ring members, consecutively attached ring members, tube members, and frames cut from solid tubes. Also, suitable frames can have a variety of sizes. The exact configuration and size chosen will depend on several factors, including the desired delivery technique, the nature of the vessel in which the device will be implanted, and the size of the vessel. A frame structure and configuration can be chosen to facilitate maintenance of the device in the vessel following implantation. The implantable frame can be formed in any suitable shape, including a ring, a stent, a tube, or a zig-zag configuration. In one example, the implantable frame can be self-expanding or balloon-expandable.

The implantable frame can be made from one or more suitable materials, including metal or polymer materials. In one aspect, the medical device includes a frame comprising a biocompatible metal or metal alloy. Examples of suitable metallic materials include, without limitation: stainless steel (such as 316 stainless steel), nickel titanium (NiTi) alloys (such as Nitinol) and other shape memory and/or superelastic materials, MP35N, gold, silver, a cobalt-chromium alloy, tantalum, platinum or platinum iridium, or other biocompatible metals and/or alloys.

The implantable frame can be formed, from a variety of medical grade polymers having properties that permit the frame to function as a supporting structure for the remodelable material. Suitable non-metallic frame materials include carbon or carbon fiber, cellulose acetate, cellulose nitrate, silicone, cross-linked polyvinyl alcohol (PVA) hydrogel, cross-linked PVA hydrogel foam, polyamide, styrene isobutylene-styrene block copolymer (Kraton), polyethylene terephthalate, polyurethane, polyamide, polyester, polyorthoester, polyanhydride, polyether sulfone, polycarbonate, polypropylene, high molecular weight polyethylene, polytetrafluoroethylene, or other biocompatible polymeric material, or mixture of copolymers thereof.

Optionally, the implantable frame may comprise a bioabsorbable or remodelable material. The implantable frame can comprise a bioabsorbable material that can be degraded and absorbed by the body over time to advantageously eliminate a frame structure from the vessel before, during or after the remodeling process. A number of bioabsorbable homopolymers, copolymers, or blends of bioabsorbable polymers are known in the medical arts. These include, but are not necessarily limited to, polyesters, poly(amino acids), copoly(etheresters), polyamides, poly(iminocarbonates), polyorthoesters, polyoxaesters, polyamidoesters, polyoxaesters containing amido groups, poly(anhydrides), polyphosphazenes, poly-alpha-hydroxy acids, poly-beta-hydroxy acids, polyorganophosphazines, polyesteramides, polyester-ethers, polyphosphoesters, polyphosphoester urethane, cyanoacrylates, polyalkylene oxalates, polyvinylpyrolidone, polyglycols, aliphatic polyesters, poly(ester-amides), modified polysaccharides and modified proteins.

Some specific examples of bioabsorbable materials include polymers and co-polymers comprising a polylactic acid, a polyglycolic acid, a polycaprolactone or derivatives thereof. Other suitable bioabsorbable materials for a frame include: poly(trimethylene carbonate), polyvinyl alcohol, poly-N-(2-hydroxypropyl)-methacrylamide, polyethylene oxide, poly(epsilon-caprolactone), poly(dimethyl glycolic acid), poly(hydroxy butyrate), polydioxanone, polyethylene oxide-polylactic acid copolymers (PEO/PLA), polylactic acid (PLA), poly(lactide-co-glycolide), poly(hydroxybutyrate-co-valerate), poly(glycolic acid-co-trimethylene carbonate), poly(epsilon-caprolactone-co-p-dioxanone), poly-L-glutamic acid or poly-L-lysine, polyhydroxyvalerate, fibrinogen, starch, collagen, hyaluronic acid, hydroxyethyl starch, and gelatin. A frame may also comprise one or more naturally derived bioabsorbable polymers, including modified polysaccharides such as cellulose, chitin, and dextran or modified proteins such as fibrin and casein.

In some examples, the implantable frames impart radially outward directed force during deployment, whether self-expanding or radially-expandable. The radially outward directed force can serve to hold the body lumen open against a force directed radially inward, as well as preventing restriction of the passageway through the lumen by intimal flaps or dissections generated by, such as prior balloon angioplasty. Another function of the radially outward directed force can also fix the position of the stent within the body lumen by intimate contact between the stent and the walls of the lumen. Preferably, the outwardly directed forces do not traumatize the lumen walls.

Preferably, the frame is self-expanding. Upon compression, self-expanding frames can expand toward their pre-compression geometry. In some examples, a self-expanding frame can be compressed into a low-profile delivery conformation and then constrained within a delivery system for delivery to a point of treatment in the lumen of a body vessel. At the point of treatment, the self-expanding frame can be released and allowed to subsequently expand to another configuration. In certain examples, the frame is formed partially or completely of alloys such as nitinol (NiTi) which have superelastic (SE) characteristics. However, while some examples provide frames made from shape memory materials, other examples comprise other materials such as stainless steel, MP35N and other suitable materials. Some examples provide frames that are not self-expanding, or that do not comprise superelastic materials.

The frame preferably includes projections, such as barbs, that maintain the frame in position following implantation in a body vessel. The art provides a wide variety of structural features that are acceptable for use in the medical device, and any suitable structural feature can be used. Furthermore, barbs can also comprise separate members attached to the frame by suitable attachment means, such as welding and bonding. For instance, barbs can be formed by V-shaped cuts transversing the thickness of a flat metal frame, which are bent outward to form the barb. In some examples, the number, arrangement, and configuration of the integral barbs can vary according to design preference and the clinical use of the device. The barbs can have any suitable shape, including points or "fish hook"-like configurations. The barbs may or may not penetrate the vein wall, depending on their design and other factors, including the thickness and type of covering used.

Also provided are examples where the frame comprises a means for orienting the frame within a body lumen. For example, the frame can comprise a marker, such as a radiopaque portion of the frame that would be seen by remote imaging methods including X-ray, ultrasound, Magnetic Resonance Imaging and the like, or by detecting a signal from or corresponding to the marker. In other examples, the delivery device can comprise a frame with indicia relating to the orientation of the frame within the body vessel. In other examples, indicia can be located, for example, on a portion of a delivery catheter that can be correlated to the location of the frame within a body vessel. A frame or delivery device may comprise one or more radiopaque materials to facilitate tracking and positioning of the medical device, which may be added in any fabrication method or absorbed into or sprayed onto the surface of part or all of the medical device. The degree of radiopacity contrast can be altered by implant content. Radiopacity may be imparted by covalently binding iodine to the polymer monomeric building blocks of the elements of the implant. Common radiopaque materials include barium sulfate, bismuth subcarbonate, and zirconium dioxide. Other radiopaque elements include: cadmium, tungsten, gold, tantalum, bismuth, platinum, iridium, and rhodium. In one preferred example, iodine may be employed for its radiopacity and antimicrobial properties. Radiopacity is typically determined by fluoroscope or x-ray film. Various other ways to incorporate radiopaque material in a medical device are provided in copending application Ser. No. 10/787,307, filed Feb. 26, 2004 by Case et al., entitled "Prosthesis Adapted for Placement Under External Imaging," which is incorporated herein by reference. Imagable markers, including radiopaque material, can be incorporated in any portion of a medical device. For example, radiopaque markers can be used to identify a long axis or a short axis of a medical device within a body vessel. For instance, radiopaque material may be attached to a frame or woven into portions of the valve member material.

Methods of Manufacturing

A method of making an implantable medical device can comprise providing a frame and covering the frame with a removable material. The removable materials can be first mixed in liquid form, forming a solution that can be applied to the surface of the frame in a manner permitting removal of the solvent and deposition of the removable material in a solid form. Solvents may be used to achieve the solution, such as water, water-dispersible polymers, tetrahydrofuran, alcohols, dichloromethane, methanol, acetone or other solvents.

The deposition of the removable material onto the surface of the frame can be performed using any conventional coating processes, for example immersion or dip coating, air knife coating, spray coating or a combination thereof. For dip coating, the portion of the frame to be coated is dipped into the coating solution, and then removed. For air knife coating, the coating is applied, and the excess is "blown off" by a powerful jet from an air knife. For spray coating, the coating solution may be applied to the frame, barb, or portion thereof using any commercial spray coater equipment. Spray coating equipment variables can be manipulated by one skilled in the art to form a suitable removable material layer.

The thickness of the resulting removable material may depend on the concentration of the coating solution and the number of layers of removable material applied. Multiple coating layers may be applied to achieve a desired thickness. The removable material preferably has a thickness sufficient to provide a desirable level of durability, but thin enough to permit sufficiently rapid dissolution of the removable material within a body vessel. For example, the removable material can have a thickness of between about 10 µm and 1 mm, including 10, 50, 100, 250, 500, 750 and 1,000 µm (1 mm). The removable material can form a coating over the entire surface of an implantable frame, or only over portions of the frame such as over projections or only the edges of projections from the frame.

A drying phase may be employed after the coating is applied such as air drying, baking, vacuum drying or dehydrating, for example, with a circulating warm gas such as air or nitrogen or other inert gas. Drying of the solution and or coating can carried out in a high-temperature air-bath using a drying oven, drying tunnel, vacuum drier, or any other suitable drying equipment.

In some examples, a bioabsorbable suture or sheath can be used to maintain a medical device in a compressed configuration both prior to and after deployment. As the bioabsorbable sheath or suture is degraded by the body after deployment, the medical device can expand within the body vessel. In some examples, a portion of the medical device can be restrained with a bioabsorbable material and another portion allowed to expand immediately upon implantation. For example, a self-expanding frame can be partially restrained by a bioabsorbable material upon deployment and later expand as the bioabsorbable material is absorbed.

Methods of manufacture may also comprise the step of attaching a first valve member to a frame. The valve member can be responsive to the flow of fluid through the frame, and adapted to permit fluid flow through said vessel in a first direction or substantially prevent fluid flow through said vessel in a second, opposite direction. The frame can have a longitudinal axis, a first radial compressibility along a first radial direction that is less than a second radial compressibility along a second radial direction.

Percutaneous Delivery of Medical Devices

In some examples, the medical devices can be configured for delivery to a body vessel. Preferably, the medical device is implanted in a radially compressed configuration, and radially expanded at a point of treatment within a body vessel. The overall configuration, cross-sectional area, and length of a medical device frame having a tubular configuration (compressed or expanded) may depend on several factors, including the size and configuration of device, the size and configuration of the vessel in which the device will be implanted, the extent of contact between the device and the walls of the vessel, and the amount of retrograde flow through the vessel that is desired.

In some examples, implantable frames can be intraluminally delivered inside the body by a catheter that supports the implantable frame in a compacted form as it is transported to the desired site, for example within a body vessel. Upon reaching the site, the implantable frame can be expanded and securely placed within the body vessel, for example by securely engaging the walls of the body vessel lumen. The expansion mechanism may involve forcing the stent to expand radially outward, for example, by inflation of a balloon formed in the distal portion of the catheter, to inelastically deform the stent and fix it at a predetermined expanded position in contact with the lumen wall. The expansion balloon can then be deflated and the catheter removed. In another technique, the implantable frame is formed of a material that will self-expand after being compacted. During introduction into the body, the implantable frame is restrained in the compacted condition. When the stent has been delivered to the desired site for implantation, the restraint is removed, allowing the implantable frame to self-expand by its own internal elastic restoring force. Once the implantable frame is located at the constricted portion of the lumen, the sheath is removed to expose the stent, which is expanded so it contacts the lumen wall. The catheter is subsequently removed from the body by pulling it in the proximal direction, through the larger lumen diameter created by the expanded prosthesis, which is left in the body.

Figure 7:
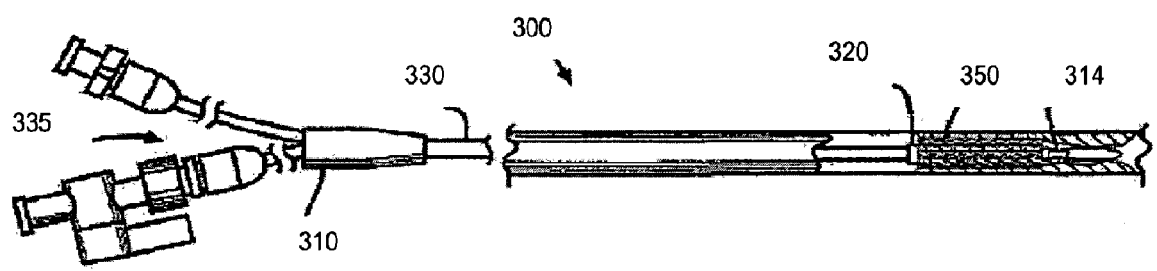
FIG. 7 is a schematic of a transcatheter delivery system for an intraluminally implantable medical device.

FIG. 7 is a schematic of a transcatheter delivery system for an intraluminally implantable medical device. The medical device may include an implantable frame designed to be percutaneously delivered through a body lumen to a target site. The target site may be, for example, a location in the venous system adjacent to an insufficient venous valve. The implantable frames may be delivered, for example, on their own or as part of an implantable prosthetic valve. FIG. 7 illustrates a delivery system 300. The delivery system 300 includes a catheter 310 having a distal end 314. A balloon 320 is positioned on the distal end 314 of the catheter 310. A connector assembly 330 is disposed at the proximal end 335 of the catheter 310 and is adapted to facilitate expansion of the balloon 320 as is known in the art. The connector assembly 330 provides access to an interior lumen of the catheter 310 to provide access to the balloon 320, and possibly a guidewire (not illustrated) or other conventional component. A balloon expandable frame 350 according to the present disclosure is disposed on the distal end 314 of the catheter 310. The expandable frame 350 surrounds the balloon 320 and is initially, prior to placement in a body vessel, in its unexpanded state. This positioning allows the balloon 320, upon inflation, to radially expand the expandable frame 350 into its expanded state. Alternatively, a self-expanding medical device frame can be compressed to a delivery configuration within a retaining sheath that is part of a catheter delivery system. Upon delivery, the radially compressed configuration can be expanded, for example, by removing a self-expanding frame, or portion thereof, from the sheath or by inflating a balloon from inside the medical device. The frame can be maintained in the radially compressed configuration prior to deployment of the medical device by any suitable means, including a sheath, a suture, a tube or other restraining material around all or part of the compressed medical device, or other methods.

As indicated above, the present disclosure is well-suited for providing artificial support to a body vessel in need of such support. This can be performed by inserting the distal end 314 of the catheter 310 into a body vessel and navigating the distal end 314, and the surrounding expandable frame 350, to a point in a vessel in need of radial support. The catheter 310 can be placed over a guidewire (not illustrated) to facilitate navigation. Once the expandable frame 350 is at the point of treatment, the balloon 320 can be inflated in the conventional manner. Inflation of the balloon 320 forces the expandable frame 350 to expand. During expansion, in which the expandable frame 350 changes from a radially compressed state to a radially expanded state. Following expansion, the balloon 320 can be deflated, leaving the expandable frame 350 in its expanded state. The catheter 310 can then be withdrawn from the vessel, leaving the expandable frame 350 in its expanded state at the point of treatment within the body vessel.

Implantable frames or prostheses comprising the implantable frame can be delivered into a body lumen using a system which includes a catheter. An appropriately sized delivery catheter can be selected by one skilled in the art for a given application. For example, some examples can be delivered using a delivery catheter selected from one or more delivery catheter sizes from the group consisting of: 1, 2, 3, 4, 5, 6, 7, 8, 9, 10, 11, 12, 13, 14, 15, 16, 17, 18, 19, 20, 21, 22, 23, 24, 25, 26, 27, 28, 29 and 30 French (F) delivery catheters, or increments of 0.1 F therebetween. In some examples, a delivery catheter sized between 1 and 25 F, or preferably between about 1.5 F and 5 F can be used, preferably a 1.8 F (0.60 mm), 2.0 F (0.66 mm), 2.3 F (0.75 mm), 2.6 F (0.85 mm), 2.7 F (0.9 mm), 2.9 F (0.95 mm), or 3.3 (1.10 mm) delivery catheters.

The implantable frames can be placed in any medically appropriate location for a given application. For example, in some examples, the implantable frame can serve as part of a venous valve prosthetic and be implanted in the femoral vein, including at the proximal (groin), mid (mid section) or distal (adjacent to the knee) portions of the vein.

Methods of Treatment

Also provided are methods of treating a patient. In one example the method comprises a step of delivering a medical device as described herein to a point of treatment in a body vessel, and deploying the medical device at the point of treatment. Additionally, the medical device can comprise a frame and a removable material.

Methods for treating certain conditions are also provided, such as venous valve insufficiency, varicose veins, esophageal reflux, restenosis or atherosclerosis. In some aspects, the disclosure relates to methods of treating venous valve related conditions. A "venous valve related condition" is any condition presenting symptoms that can be diagnostically associated with improper function of one or more venous valves. In mammalian veins, natural valves are positioned along the length of the vessel in the form of leaflets disposed annularly along the inside wall of the vein which open to permit blood flow toward the heart and close to prevent back flow. These natural venous valves act as open to permit the flow of fluid in the desired direction, and close upon a change in pressure, such as a transition from systole to diastole. When blood flows through the vein, the pressure forces the valve leaflets apart as they flex in the direction of blood flow and move towards the inside wall of the vessel, creating an opening therebetween for blood flow. Functioning leaflets return to a closed position to restrict or prevent blood flow in the opposite, i.e. retrograde, direction after the pressure is relieved. The leaflets, when functioning properly, extend radially inwardly toward one another such that the tips contact each other to block backflow of blood. Two examples of venous valve related conditions are chronic venous insufficiency and varicose veins.

On occasion, and for a variety of reasons, such as congenital valve or vein weakness, disease in the vein, obesity, pregnancy, and/or an occupation requiring long periods of standing, one or more valves in a vein will allow deleterious retrograde flow to occur. When a valve allows such retrograde flow, blood will collect, or pool in vessels beneath the valve. This pooling of blood causes an increase in the venous pressure below the valve. Venous valves that allow such deleterious retrograde flow are known as incompetent or inadequate venous valves. The condition resulting from such incompetent venous valves is known as venous valve insufficiency. In the condition of venous valve insufficiency, the venous valve leaflets do not function properly. Incompetent venous valves can cause the veins to bulge, can cause swelling in the patient's lower extremities, and can result in varicose veins and/or chronic venous insufficiency. If left untreated, venous valve insufficiency can cause venous stasis ulcers of the skin and subcutaneous tissue.

In the condition of venous valve insufficiency, the valve leaflets do not function properly. For example, the vein can be too large in relation to the leaflets so that the leaflets cannot come into adequate contact to prevent backflow (primary venous valve insufficiency), or as a result of clotting within the vein that thickens the leaflets (secondary venous valve insufficiency). Incompetent venous valves can result in symptoms such as swelling and varicose veins, causing great discomfort and pain to the patient. If left untreated, venous valve insufficiency can result in excessive retrograde venous blood flow through incompetent venous valves, which can cause venous stasis ulcers of the skin and subcutaneous tissue. Venous valve insufficiency can occur, for example, in the superficial venous system, such as the saphenous veins in the leg, or in the deep venous system, such as the femoral and popliteal veins extending along the back of the knee to the groin.

The varicose vein condition consists of dilatation and tortuousity of the superficial veins of the lower limb and resulting cosmetic impairment, pain and ulceration. Primary varicose veins are the result of primary incompetence of the venous valves of the superficial venous system. Secondary varicose veins occur as the result of deep venous hypertension which has damaged the valves of the perforating veins, as well as the deep venous valves. The initial defect in primary varicose veins often involves localized incompetence of a venous valve thus allowing reflux of blood from the deep venous system to the superficial venous system. This incompetence is traditionally thought to arise at the saphenofemoral junction but may also start at the perforators. Thus, gross saphenofemoral valvular dysfunction may be present in even mild varicose veins with competent distal veins. Even in the presence of incompetent perforation, occlusion of the saphenofemoral junction usually normalizes venous pressure.

The initial defect in secondary varicose veins is often incompetence of a venous valve secondary to hypertension in the deep venous system. Since this increased pressure is manifested in the deep and perforating veins, correction of one site of incompetence could clearly be insufficient as other sites of incompetence will be prone to develop. However, repair of the deep vein valves would correct the deep venous hypertension and could potentially correct the secondary valve failure. Apart from the initial defect, the pathophysiology is similar to that of varicose veins.

Accordingly, methods of treating a venous valve related condition may comprise the step of providing one or more medical devices comprising implantable frames as described herein. Methods of treatment may comprise the step of providing one or more frames attached to one or more valve leaflets. In some examples, methods of treatment may also include the steps of delivering a medical device to a point of treatment in a body vessel, and deploying a medical device at the point of treatment, where the medical devices are as described herein. Such medical devices can be inserted intravascularly, for example from an implantation catheter. The medical devices can function as a replacement venous valve, or enhance venous valve function by bringing incompetent valve leaflets into closer proximity. In one procedure, venous valve function can be provided by an implanted medical device.

Figure 8:
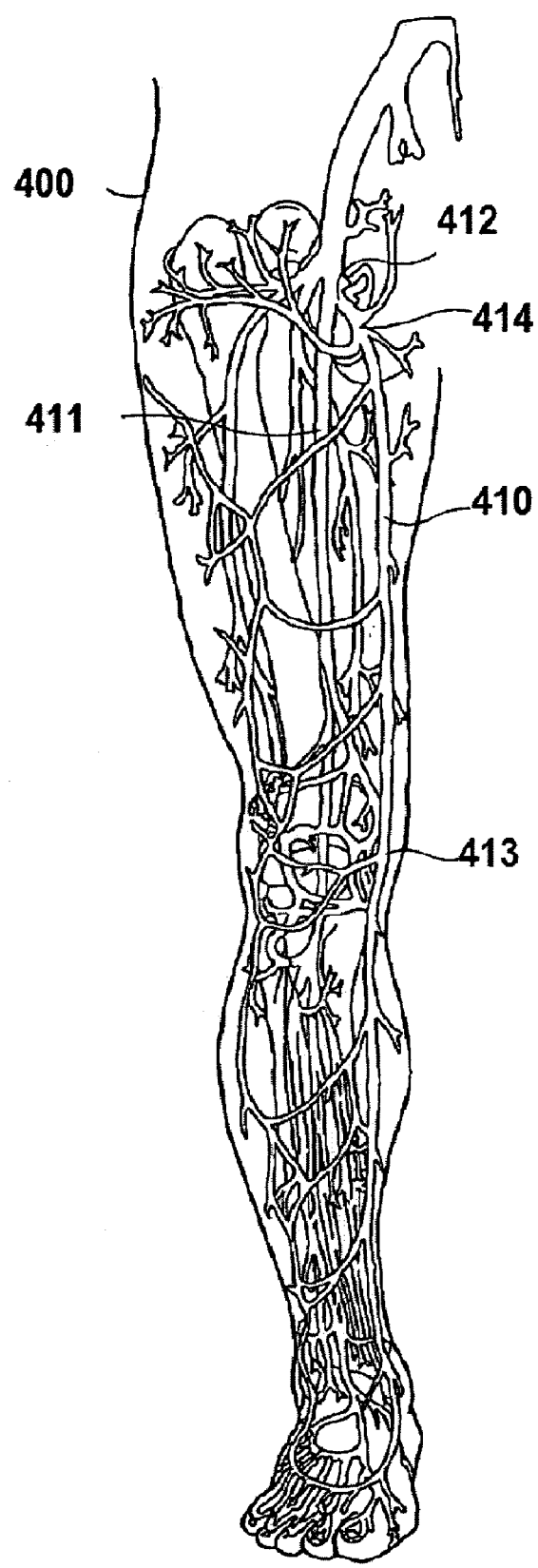
FIG. 8 is a diagram of a human leg showing certain venous structures therein.

FIG. 8 is a diagram of a human leg 400 showing certain venous structures therein. In particular, shown is human leg 400 having GSV 410 and femoral vein 411 which adjoin at the sapheno-femoral junction 412. In accordance with certain methods of treatment, a medical device comprising an implantable frame may be placed in the GSV 410 between a point 413 occurring near the medial side of the knee and a point 414 occurring prior to the sapheno-femoral junction 412. Desirably, the medical device functions as a valve to prevent or reduce reflux of venous blood from the sapheno-femoral junction 412 in a direction down toward the medial side of the knee (e.g. at point 413). Such occlusion may be effective to treat varicosities that commonly occur in lower portions of the leg, e.g. portions occurring below the knee.

The medical device is preferably implanted from a delivery catheter via percutaneous access to the GSV 410, for example by the Seldinger technique or any other suitable technique. For instance, an access needle (not shown) can be passed through the skin to access the GSV 410, and a wire guide can be passed through the access needle and into the vein. Prior to deployment of an inverted occlusion device (not shown), wire guide can be used for any number of conventional procedures including catheterization and imaging procedures in order to locate the sapheno-femoral junction. After any such preliminary procedures that are performed, the wire guide can be used in a deployment procedure for an inflatable occlusion device.

Methods for delivering a medical device as described herein to any suitable body vessel are also provided, such as a vein, artery, billiary duct, ureteral vessel, body passage or portion of the alimentary canal.

While various aspects and examples have been described, it will be apparent to those of ordinary skill in the art that many more examples and implementations are possible within the scope of the disclosure. Accordingly, the disclosure is not to be restricted except in light of the attached claims and their equivalents.

We claim:

1. A medical device for implantation in a body vessel, comprising:
    an implantable frame comprising a plurality of struts interconnected with a plurality of bends, a first strut of the plurality of struts extending between first and second bends of the plurality of bends and comprising a straight section of the frame free of other bends and of intersections with other struts of the plurality of struts, the straight section defining a surface and a plurality of projections extending from the surface, the plurality of projections having first and second projections and the surface having a portion positioned between the first and second projections;
    each of the first and second projections including a beveled edge and having a cross-sectional area at the intersection of the projection and the surface that is less than about 10 mm$^2$; and
    a biocompatible removable material enclosing the beveled edge of the first projection and the beveled edge of the second projection;
    the portion of the surface positioned between the first and second projections being free of the biocompatible removable material.

2. The medical device of claim 1, where the biocompatible removable material is water-soluble.

3. The medical device of claim 1, where the biocompatible removable material encloses the first and second projections.

4. The medical device of claim 1, where the biocompatible removable material enclosing the beveled edge of the first and second projections is between about 1 μm and 1 mm thick.

5. The medical device of claim 1, where each of the first and second projections of the plurality of projections comprises a substantially triangular, substantially square, substantially rectangular, substantially elliptical, or substantially semi-circular cross-sectional shape at the intersection of the first and second projections and the surface.

6. The medical device of claim 1, where each projection of the plurality of projections comprises a barb configured to engage the wall of a body vessel.

7. The medical device of claim 1, where each projection of the plurality of projections comprises a barb enclosed by a biocompatible removable material.

8. The medical device of claim 1, where the implantable frame has a tubular configuration that is moveable from a radially compressed state to a radially expanded state.

9. The medical device of claim 1, where the implantable frame comprises a material selected from the group consisting of: a nickel-titanium alloy, a cobalt-chromium alloy, and stainless steel.

10. The medical device of claim 1, where the medical device is an implantable valve further comprising at least one valve leaflet attached to the implantable frame, the implantable frame comprising a plurality of struts and bends defining a substantially cylindrical lumen and having a plurality of projections configured as barbs attached to the implantable frame.

11. The medical device of claim 1, wherein the implantable frame defines a substantially cylindrical lumen having a lengthwise axis and each of the first and second projections extends radially outward relative to the lengthwise axis.

12. The medical device of claim 1, wherein the implantable frame defines a substantially cylindrical lumen having a lengthwise axis and each of the first and second projections extends outward from the frame along a line that is substantially parallel to the lengthwise axis.

13. A medical device for implantation in a body vessel, comprising:
    an implantable frame comprising a plurality of struts and bends defining a substantially cylindrical lumen, a first strut of the plurality of struts extending between first and second bends and comprising a straight section of the frame free of other bends and of intersections with other struts of the plurality of struts, the straight section defining a surface having a first portion and a second portion;
    the first portion comprising a plurality of barbs extending from the surface, the plurality of barbs comprising at least first and second barbs, and the second portion comprising a portion of the surface positioned between the first and second barbs and having no barbs;
    each barb of the plurality of barbs having a cross-sectional area at the intersection of the barb and the implantable frame surface that is less than about 10 mm$^2$;
    a water-soluble biocompatible removable material enclosing at least one of the plurality of barbs and having a thickness between about 10 μm and about 1 mm; and
    the second portion being free of the biocompatible removable material.

14. A medical device for implantation in a body vessel, comprising:
    an implantable frame comprising a plurality of struts interconnected with a plurality of bends, a first strut of the plurality of struts extending between first and second bends of the plurality of bends and comprising a straight section of the frame free of other bends and of intersections with other struts of the plurality of struts, the straight section comprising a surface and a plurality of projections extending from the surface, the plurality of projections having first and second projections and the surface having a portion positioned between the first and second projections;
    each of the first and second projections having a height and including a beveled edge and having a cross-sectional area at the intersection of the projection and the surface that is less than about 10 mm$^2$; and
    a biocompatible removable material positioned on the portion of the surface positioned between the first and second projections and having a thickness that is greater than the height of the first and second projections.

15. The medical device of claim 14, where the biocompatible removable material is water-soluble.

16. The medical device of claim 14, where the biocompatible removable material enclosing the beveled edge of the first and second projections is between about 1 μm and 1 mm thick.

17. The medical device of claim 14, where the implantable frame has a tubular configuration that is moveable from a radially compressed state to a radially expanded state.

18. The medical device of claim 14, where the implantable frame comprises a material selected from the group consisting of: a nickel-titanium alloy, a cobalt-chromium alloy, and stainless steel.

19. The medical device of claim 14, where the medical device is an implantable valve further comprising at least one valve leaflet attached to the implantable frame, the implantable frame comprising a plurality of struts and bends defining a substantially cylindrical lumen and having a plurality of projections configured as barbs attached to the implantable frame.

20. The medical device of claim 14, wherein the frame defines a substantially cylindrical lumen having a lengthwise axis and each of the first and second projections extends radially outward relative to the lengthwise axis.

21. The medical device of claim 14, wherein the frame defines a substantially cylindrical lumen having a lengthwise axis and each of the first and second projections extends outward from the frame along a line that is substantially parallel to the lengthwise axis.

* * * * *